US00PP32751P2

(12) United States Plant Patent
Mimoto

(10) Patent No.: US PP32,751 P2
(45) Date of Patent: Jan. 12, 2021

(54) ***AJUGA* PLANT NAMED 'GOLD CHANG'**

(50) Latin Name: *Ajuga reptans*
Varietal Denomination: Gold Chang

(71) Applicant: Osco Garden B.V., Aalsmeer (NL)

(72) Inventor: Kazuo Mimoto, Kochi (JP)

(73) Assignee: OSCO GARDEN B.V., Aalsmeer (NL)

( * ) Notice: Subject to any disclaimer, the term of this patent is extended or adjusted under 35 U.S.C. 154(b) by 0 days.

(21) Appl. No.: 16/873,508

(22) Filed: Apr. 24, 2020

(51) Int. Cl.
*A01H 5/02* (2018.01)
*A01H 6/00* (2018.01)

(52) U.S. Cl.
USPC ..... Plt./401

(58) Field of Classification Search
USPC ..... Plt./401
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Ajuga* plant named 'Gold Chang' that is characterized by its golden yellow foliage, its compact plant habit, its full season interest because of its foliage and its flowers, its pink flowers, its unique spatulate shaped leaves, and its large flowering spikes.

2 Drawing Sheets

Botanical classification: *Ajuga reptans.*
Variety denomination: 'Gold Chang'.

CROSS REFERENCE TO A RELATED APPLICATION

This application is related to a European plant breeders' rights application filed on Jan. 16, 2019, application No. 2018/3192. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Ajuga reptans* and will be referred to hereafter by its cultivar name, 'Gold Chang'. 'Gold Chang' represents a new cultivar of *Ajuga*, an herbaceous perennial grown for landscape use.

'Gold Chang' was discovered by the Inventor as a naturally occurring meristematic mutation of an unnamed and unpatented plant of *Ajuga reptans* from the Inventor's breeding program that was growing outdoors in a trial plot in Koch-City, Japan in spring of 2016.

Asexual propagation of the new cultivar was first accomplished by the Inventor by stem cuttings in spring of 2016 in Kochi-City, Japan. Asexual propagation by stem cuttings and tissue culture using meristem tissue has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Gold Chang' as a unique cultivar of *Ajuga.*

1. 'Gold Chang' exhibits golden yellow foliage.
2. 'Gold Chang' exhibits a compact plant habit.

3. 'Gold Chang' exhibits full season interest because of its foliage and its flowers.
4. 'Gold Chang' exhibits pink flowers.
5. 'Gold Chang' exhibits a unique spatulate shaped leaves.
6. 'Gold Chang' exhibits large flowering spikes.

The female parent of 'Gold Chang' differs in having green foliage. 'Gold Chang' can be most closely compared to *Ajuga reptans* cultivars 'Page's Yellow' (not patented) and 'Golden Glow' (un patented). 'Page's Yellow' is similar to 'Gold Chang' in having foliage that is yellow in color. 'Page's Yellow' differs from 'Gold Chang' in having flowers that are blue in color, flower spikes that are smaller, and leaves that are ovate in shape and smaller in size. 'Golden Glow' is similar to 'Gold Chang' in having foliage that has some yellow coloration and a similar leaf shape. 'Golden Glow' differs from 'Gold Chang' in having foliage that is less yellow in color and changes to having reddish variegation during cold temperatures and flowers that are blue in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listing by Nova photo graphics, allegro Archives, Aga Flora, Podoslonami, Bergenia, Zielony Ogrodek, Barnes Nursery, and listings in regards to its entrance in the new plant competition by Hortweek, KVBC, Plantarium, and Plantkeuze (facebook).

BRIEF DESCRIPTION OF THE DRAWINGS

The accompanying colored photographs illustrate the overall appearance and distinct characteristics of a 4-month-old plant the new *Ajuga* as grown outdoors in a 11-cm circular container in Dobrcz, Poland.

The photograph in FIG. 1 provides a side view of 'Gold Chang' in bloom.

Figure 1:
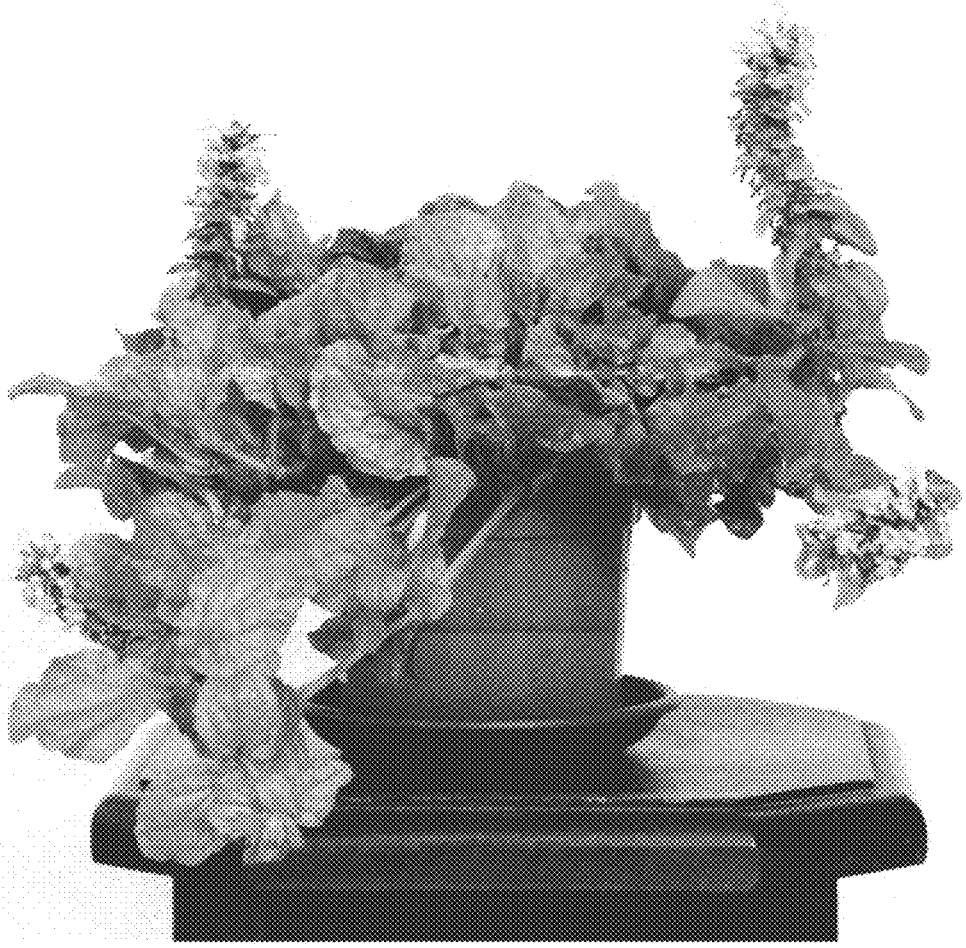
Figure 2:
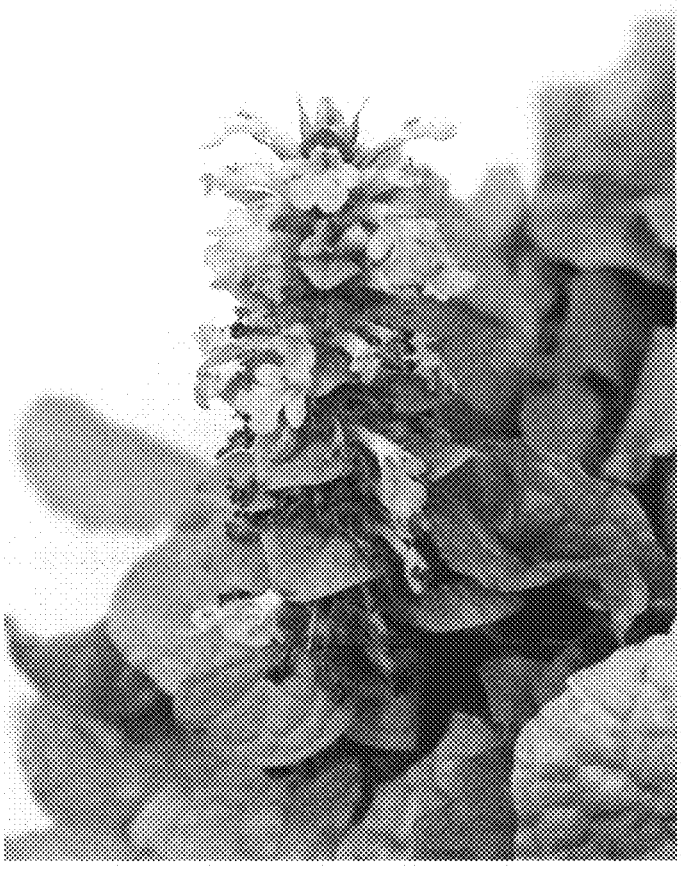

The photograph in FIG. 2 provides a close-up view of an inflorescence of 'Gold Chang'.

Figure 3:
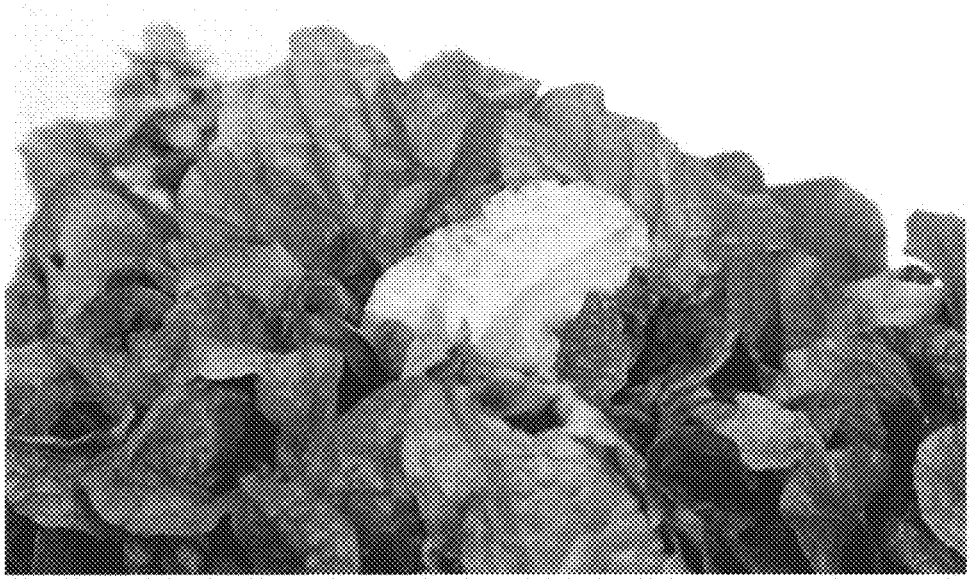

The photograph in FIG. 3 provides a close-up view of the foliage of 'Gold Chang'.

The colors in the photograph may differ slightly from the color values cited in the detailed botanical description, which accurately describe the colors of the new *Ajuga*.

DETAILED BOTANICAL DESCRIPTION

The following is a detailed description of the new cultivar as observed on 4-month-old plants as grown outdoors in 11-cm containers in Dobrcz, Poland. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—End of April to beginning of June in Japan.

*Plant type*.—Herbaceous perennial.

*Plant habit*.—Broadly spreading, creeping, compact upright inflorescences.

*Height and spread*.—Average of 10 cm in height (soil level to top of foliar plane), an average of 15 cm in height (soil level to top of floral plane) and 45 cm in spread.

*Cold hardiness*.—At least in U.S.D.A. Zone 5.

*Diseases and pests*.—No susceptibility or resistance to diseases or pests has been observed.

*Root description*.—Fine and fibrous.

*Propagation type*.—Stem cuttings and tissue culture.

*Root development*.—Rooted stem cuttings initiate in 5 to 8 days (depending of temperature and light levels) and a young plant from a rooted cutting is produced in about 6 weeks (in spring).

*Growth rate*.—Moderate.

Stem description:

*Stem shape*.—Quadrangular with obtuse angles.

*Stem color*.—Young; 146B, angles N199A, mature; 200D, angles 200C, lower surface 146D, internodes; 200D, lower surface 146D.

*Stem size*.—An average of 11.5 cm (excluding inflorescence) in length and 3 mm in diameter.

*Stem surface*.—Glossy, densely pubescent with soft hairs and average of 1 mm in length and NN155C in color.

*Stem aspect*.—Average angle of 80°.

*Internode length*.—An average of 5 cm.

*Branching habit*.—Main branches grow from the base, an average of 24 main stems and 1 lateral branch per main stem, moderately strong.

Foliage description:

*Leaf shape*.—Spathulate.

*Leaf division*.—Simple.

*Leaf base*.—Narrow cuneate.

*Leaf apex*.—Obtuse.

*Leaf venation*.—Pinnate, upper surface color 144B and 11A, lower surface color 146D and 11A.

*Leaf margins*.—Irregular angulate, strongly undulate, unlobed.

*Leaf arrangement*.—Opposite.

*Leaf surface*.—Upper surface; smooth, moderately pubescent with soft short hairs, moderately glossy, lower surface; smooth, very sparsely pubescent with soft hairs an average of 0.5 mm in length, 155A in color.

*Leaf color*.—New growth upper surface; 145A, new growth lower surface; 145A to 145B, mature upper surface; 143A and 144A, with upper half on some leaves and full leaves on others developing to 11A and 151A, mature lower surface; 145A to 146D, with upper half on some leaves and full leaves developing to 11A to 11B and 151B.

*Leaf size*.—Average of 7.5 cm in length, 4.4 cm in width.

*Leaf quantity*.—Average of 14 per lateral stem.

*Leaf attachment*.—Petiolate.

*Petioles*.—Average of 4.1 cm in length, 5 mm in diameter at the widest point and 2.5 mm at the narrowest point, both sides smooth and glossy, margins are moderately covered with soft short hairs 0.5 mm in length and NN155C in color, very strong, color; upper surface 145B, margins 144B, color changing to 185D, lower surface 146D, margins 144A, color changing to 185D.

Flower description:

*Inflorescence type*.—Raceme, individual flowers in clusters of 7 flowers in leaf-axils.

*Inflorescence size*.—An average of 9.6 cm in height and 3 cm in width.

*Inflorescence number*.—Average of 5.

*Lastingness of inflorescence*.—Average of 10 days, self-cleaning.

*Flower type*.—Labiate, single.

*Flower number*.—Average of 150 per inflorescence and 750 per plant.

*Flower fragrance*.—None.

*Flower buds*.—Oblong in shape, average of 7 mm in length and 2.5 mm in diameter, color; 73D, immature sepals 148D, surface matte and densely covered with short hairs; an average of 1 mm in length and NN155D in color.

*Flower size*.—Average of 8 mm in height, 7 mm in diameter and 1.4 cm in length, throat diameter 2 mm, tube 8 mm in length and 2 mm in diameter.

*Peduncles*.—An average of 8.3 cm in length, 3 mm in diameter, held straight on top of lateral branch, moderately strong, color; 148A, surface is moderately glossy and densely covered with very short hairs; an average of 1.25 mm in length and NN155C in color.

*Pedicels*.—An average of 0.5 mm in length and diameter, held in an average angle of 45° from peduncle, moderately strong, 148A in color, surface is slightly glossy and moderately covered with very short hairs; an average of 0.3 mm in length and too small to measure color.

*Calyx*.—Rotate and tubular in shape, 5 mm in length, 3 mm in diameter.

*Sepals*.—5, 1 whorl, average of 4.5 mm in length, 2 mm in width, ovate in shape, 55% of base fused into tube, acute apex, entire margins, color; when opening and fully open upper surface 91A, when opening lower surface 86C, when fully open lower surface 90D, upper surface smooth and glabrous, matte, lower surface moderately pubescent with short hairs; an average of 0.75 mm in length and NN155D in color.

*Petals*.—Average of 5, 1 whorl, petals fused into tube, upper petals; average of 1 cm in length, 1.5 mm in width, oblanceolate in shape, obtuse apex, entire margins, low undulation, upper surface smooth and glabrous, both surfaces sparsely covered with very short hairs; an average of 0.3 mm in length and NN155D in color, lower petals; average of 6.5 mm in length, 6 mm in width, obcordate in shape, apex is obtuse with lower petal cleft 2-lobed, entire margins, no undulation, upper surface smooth and glabrous, both surfaces sparsely covered with very short hairs; an average of 0.3 mm in length and NN155D in color, flower throat texture is smooth and glabrous, flower tube texture upper (inner) side is smooth and glabrous, flower tube texture outer side is moderately pubescent with very short hairs; an average of 0.75 mm in length and NN155D in color, color when opening and fully open upper surface; upper petals 76D, lateral petals 75C, lower petals 73B, base 75C, veins on lateral petals 75A, color when opening and fully open lower surface; all petals 75C, lower petal tinged 75B at the top, veins on lateral petals 75A, throat color 75C, tube color 76C.

Reproductive organs:

*Pistils*.—1, style; 9.5 mm in length, 94D in color, stigma; 0.2 mm in length, cleft in shape, 76B to 76C in color, ovary; 144B in color.

*Stamens*.—4, filament; implanted into flower tube, two filaments longer, two are shorter, average length of short filaments is 3 mm, average length of longer filaments is 4 mm, N155A in color, anthers; dorsifixed, short oblong in shape, 0.5 mm in length, 0.4 mm in width and 202A in color, pollen; moderate in quantity and 14B in color.

*Fruit/seeds*.—None produced to date.

It is claimed:

1. A new and distinct variety of *Ajuga* plant named 'Gold Chang' as described and illustrated herein.

* * * * *